(12) United States Patent
Oates et al.

(10) Patent No.: US 8,424,514 B2
(45) Date of Patent: Apr. 23, 2013

(54) FLOW GENERATOR MESSAGE SYSTEM

(75) Inventors: John David Oates, Stanhope Gardens (AU); Mark David Buckley, Buchendorf (DE); Philip Rodney Kwok, Chatswood (AU); Mark Alexander Abourizk, Boronia Park (AU); Thomas Evan Miller, Churchville, NY (US); Simone Marie Jeha, Killara (AU); Mark John Payne, Basel (CH); Muditha Pradeep Dantanarayana, Cherrybrook (AU)

(73) Assignee: ResMed Limited, Bella Vista (AU)

( * ) Notice: Subject to any disclaimer, the term of this patent is extended or adjusted under 35 U.S.C. 154(b) by 1153 days.

(21) Appl. No.: 12/067,234

(22) PCT Filed: Oct. 13, 2006

(86) PCT No.: PCT/AU2006/001506
§ 371 (c)(1),
(2), (4) Date: Nov. 14, 2008

(87) PCT Pub. No.: WO2007/041797
PCT Pub. Date: Apr. 19, 2007

(65) Prior Publication Data
US 2009/0120437 A1    May 14, 2009

Related U.S. Application Data

(60) Provisional application No. 60/726,178, filed on Oct. 14, 2005.

(51) Int. Cl.
*A61M 16/00* (2006.01)
(52) U.S. Cl.
USPC ................. 128/200.24; 128/200.21

(58) Field of Classification Search ............... 128/200.4, 128/204.26, 202.22, 203.12, 204.23
See application file for complete search history.

(56) References Cited

U.S. PATENT DOCUMENTS 2,598,978 A    6/1952  Martin
5,844,862 A   12/1998  Cocatre-Zilgien
(Continued)

FOREIGN PATENT DOCUMENTS

EP    1 449 558      8/2004
WO    WO 97/06843    2/1997
(Continued)

OTHER PUBLICATIONS

Amended Notice of Opposition to Grant of Patent and Statement of Case issued Feb. 29, 2012 for corresponding New Zealand Application No. 567371 (20 pages).

(Continued)

*Primary Examiner* — Jerome W Donnelly
(74) *Attorney, Agent, or Firm* — Nixon & Vanderhye, PC

(57) ABSTRACT

A flow generator for delivering breathable gas to a patient includes a processor coupled with operation sensors and a user interface. The processor is programmed to generate at least one of time-based or event-based messages relating to at least one of flow generator operation, flow generator service, flow generator use, patient health, peripheral devices and services, patient treatment, and reminders. Time-based messages are generated at predetermined time intervals based on either time of use or elapsed time. The event-based messages are generated based on signals from the operation sensors. The user interface is configured to deliver the messages to at least one of a display, a flow generator service provider, the patient and a physician. By this system, operation of the flow generator is facilitated and enhanced.

58 Claims, 2 Drawing Sheets

U.S. PATENT DOCUMENTS

| | | | |
|---|---|---|---|
| 5,895,595 | A | 4/1999 | Haden |
| 6,119,686 | A | 9/2000 | Somerson et al. |
| 6,360,741 | B2 | 3/2002 | Truschel |
| 6,425,395 | B1 | 7/2002 | Brewer et al. |
| 6,546,930 | B1 | 4/2003 | Emerson et al. |
| 6,678,215 | B1 | 1/2004 | Treyz et al. |
| 2002/0022973 | A1 | 2/2002 | Sun et al. |
| 2002/0088464 | A1 | 7/2002 | Truschel |
| 2003/0076745 | A1 | 4/2003 | Chapman |
| 2003/0187525 | A1 | 10/2003 | Mann et al. |
| 2003/0236450 | A1 | 12/2003 | Kocinski |
| 2005/0076906 | A1 | 4/2005 | Johnson |
| 2005/0114182 | A1 | 5/2005 | Randolph et al. |

FOREIGN PATENT DOCUMENTS

| | | |
|---|---|---|
| WO | WO 01/00264 | 1/2001 |
| WO | WO 01/32069 A2 | 5/2001 |
| WO | WO 2004/049912 | 6/2004 |
| WO | WO 2005/011556 A2 | 2/2005 |

OTHER PUBLICATIONS

U.S. Appl. No. 10/533,940, filed Dec. 2006, Kenyon et al.
U.S. Appl. No. 60/656,880, filed Mar. 2005, Kwok.
U.S. Appl. No. 60/703,432, filed Jul. 2005, Kwok et al.
International Search Report for PCT/AU2006/001506 mailed Jan. 30, 2007.
Written Opinion of the International Searching Authority for PCT/AU2006/001506.

FLOW GENERATOR MESSAGE SYSTEM

CROSS-REFERENCES TO RELATED APPLICATIONS

This application is the U.S. national phase of International Application No. PCT/AU2006/001506 filed Oct. 13, 2006 which designated the U.S. and claims the benefit of U.S. Provisional Application No. 60/726,178, filed Oct. 14, 2005, each of which is incorporated herein by reference in its entirety.

STATEMENT REGARDING FEDERALLY SPONSORED RESEARCH OR DEVELOPMENT (Not Applicable)

BACKGROUND OF THE INVENTION

The present invention relates generally to flow generators for ventilatory assistance and, more particularly, to a flow generator that includes a message system for communicating messages relating to flow generator operation, flow generator service, flow generator use, patient health, peripheral devices and services, patient treatments, general reminders, and the like. Messages may be delivered to an onboard display or externally to a service provider, the patient, a physician, or the like.

Non-invasive Positive Pressure Ventilation (NIPPV) is a form of treatment for breathing disorders which can involve providing a relatively higher pressure of air or other breathable gas to the entrance of a patient's airways via a patient interface (e.g., a mask) during the inspiratory phase of respiration, and providing a relatively lower pressure or atmospheric pressure in the patient mask during the expiratory phase of respiration. In other NIPPV modes the pressure can be made to vary in a complex manner throughout the respiratory cycle. For example, the pressure at the mask during inspiration or expiration can be varied through the period of treatment.

Continuous Positive Airway Pressure (CPAP) treatment is commonly used to treat breathing disorders including Obstructive Sleep Apnea (OSA). CPAP treatment continuously provides pressurized air or other breathable gas to the entrance of a patient's airways via a patient interface (e.g., a mask) at a pressure elevated above atmospheric pressure, typically in the range 3-20 cm $H_2O$. CPAP treatment can act as a pneumatic splint of a patient's upper airway.

CPAP treatment can be in a number of forms, including the maintenance of a constant treatment pressure level, alternating between two different constant levels in synchronism with the inspiratory and expiratory phases of respiration ("bi-level CPAP"), and having an automatically adjustable and/or a computer controlled level in accordance with a patient's therapeutic needs.

Breathable gas supply apparatus used in CPAP and NIPPV treatments broadly comprise a flow generator constituted by a continuous source of air or other breathable gas generally in the form of a blower driven by an electric motor. A pressurized supply of air or other breathable gas can also be used. The gas supply is connected to a conduit or tube, which is in turn connected to a patient interface (mask or nasal prong) which incorporates, or has in close proximity, a vent to atmosphere for exhausting exhaled gases, such as carbon dioxide.

BRIEF SUMMARY OF THE INVENTION

Patients using flow generators necessarily integrate the devices into their sleeping routine. The devices are used on a daily basis and greatly enhance the quality of life for patients requiring them. It would thus be desirable if the flow generators themselves could communicate with the users to maximize system effectiveness and therapy and facilitate use of the device in the patients' daily lives.

In this context, it is important that the device function and be operated properly, and it is desirable to enable the device to introspectively determine operating concerns or malfunctions. The present invention provides a flow generator that generates messages to facilitate use of the device. The messages may relate to aspects of the flow generator itself or to integrating the system into a patient's daily routine. The messages can be delivered over any suitable medium in any suitable manner, such as for example by written, graphical or audible messages. A related flow generator with a patient reminder system is disclosed in U.S. patent application Ser. No. 10/533,940, the contents of which are hereby incorporated by reference.

In an exemplary embodiment of the invention, a flow generator for delivering breathable gas to a patient includes a processor coupled with operation sensors and a user interface. The processor is programmed to generate one of time-based messages, event-based messages, or both time- and event-based messages relating to at least one of flow generator operation, flow generator service, flow generator use, patient health, peripheral devices and services, patient treatment, and general reminders. The time-based messages are generated at predetermined time intervals based on either time of use or elapsed time, and the event-based messages are generated based on signals from the operation sensors. The user interface is configured to deliver the messages to at least one of a display, a flow generator service provider, the patient and a physician.

The processor is preferably programmed to receive a reminder request input, wherein the time-based messages include reminders generated at a time specified in the reminder request input. The user interface may include a wireless communication system that communicates with at least one of a preset telephone number, a cellular phone, a pager, and a call center.

In one embodiment, the user interface is a network interface that delivers the messages via a global network such as the internet. In this context, the event-based messages may comprise messages relating to flow generator parts requiring replacement or repair. Moreover, the system may automatically order at least one of the parts requiring replacement or service for the repair. The network interface is preferably also configured to receive message content via the global network. The message content may comprise information relating to new products and peripherals cooperatively usable with the flow generator.

The flow generator may additionally include a memory that stores software executed by the processor and data relating to flow generator use and operation. The processor executes the software to generate the messages. In one embodiment, the memory is a data card.

The flow generator may still additionally include peripheral devices providing enhanced functionality. The peripheral devices communicate with the processor, wherein the time-based and event-based messages relate to use and operation of the peripheral devices.

The time-based messages may be customizable, for example, providing a personal reminder for the patient, a wake-up alarm or the like. The wake-up alarm may be an audio message or may be effected via the delivery of breathable gas to the patient. The messages may include advertisements generated at predetermined time intervals and/or upon the occurrence of at least one event relating to flow generator use and operation. The messages may relate to helpful user tips and may be interactive with the patient.

The event-based messages may be structured as notice levels relating to flow generator operation, where the notice levels are changed based on a use condition duration detected by the sensors. In one embodiment, the use condition is a leak, wherein a first notice level provides an indication that the leak has been detected, a second notice level provides another indication that the leak has been detected along with user tips to correct the leak, and a third notice level provides a communication notifying a service provider or physician of the leak.

In another exemplary embodiment of the invention, a CPAP apparatus includes a flow generator that generates a supply of pressurized air to be provided at an outlet; a patient interface engageable with a patient's face to provide a seal; and an air delivery conduit coupled between the flow generator and the patient interface to deliver the supply of pressurized air from the flow generator to the patient interface. The flow generator preferably includes a processor coupled with operation sensors and a user or communication interface.

In yet another exemplary embodiment of the invention, an identifier is provided for use with a flow generator that generates a supply of pressurized air to be provided at an outlet to a patient for treatment. The flow generator includes a processor coupled with operation sensors and a user interface, wherein the processor is programmed to generate time-based and/or event-based messages relating to at least one of flow generator operation, flow generator service, flow generator use, patient health, peripheral devices and services, patient treatment, and general reminders, wherein the time-based messages are generated at predetermined time intervals based on either time of use or elapsed time, and wherein the event-based messages are generated based on signals from the operation sensors. The identifier includes an identifying element providing an identifying feature unique to a specific peripheral component attachable to the flow generator. The processor discerns the specific peripheral component via the identifying feature. In this context, the time-based and event-based messages are generated based on use and operation of the specific peripheral component.

In still another exemplary embodiment of the invention, a method is provided for operating a flow generator that generates a supply of pressurized air to be provided at an outlet to a patient for treatment, the flow generator including a processor coupled with operation sensors and a user interface. The method includes the steps of generating either time-based or event-based messages relating to at least one of flow generator operation, flow generator service, flow generator use, patient health, peripheral devices and services, patient treatment, and general reminders, the time-based messages being generated at predetermined time intervals based on either time of use or elapsed time, and the event-based messages being generated based on signals from the operation sensors; and delivering the messages via the user interface to at least one of a display, a flow generator service provider, the patient and a physician.

BRIEF DESCRIPTION OF THE DRAWINGS

These and other aspects and advantages of the present invention will be described in detail with reference to the accompanying drawings, in which.

DETAILED DESCRIPTION OF PREFERRED EMBODIMENTS

Flow Generator

Figure 1:
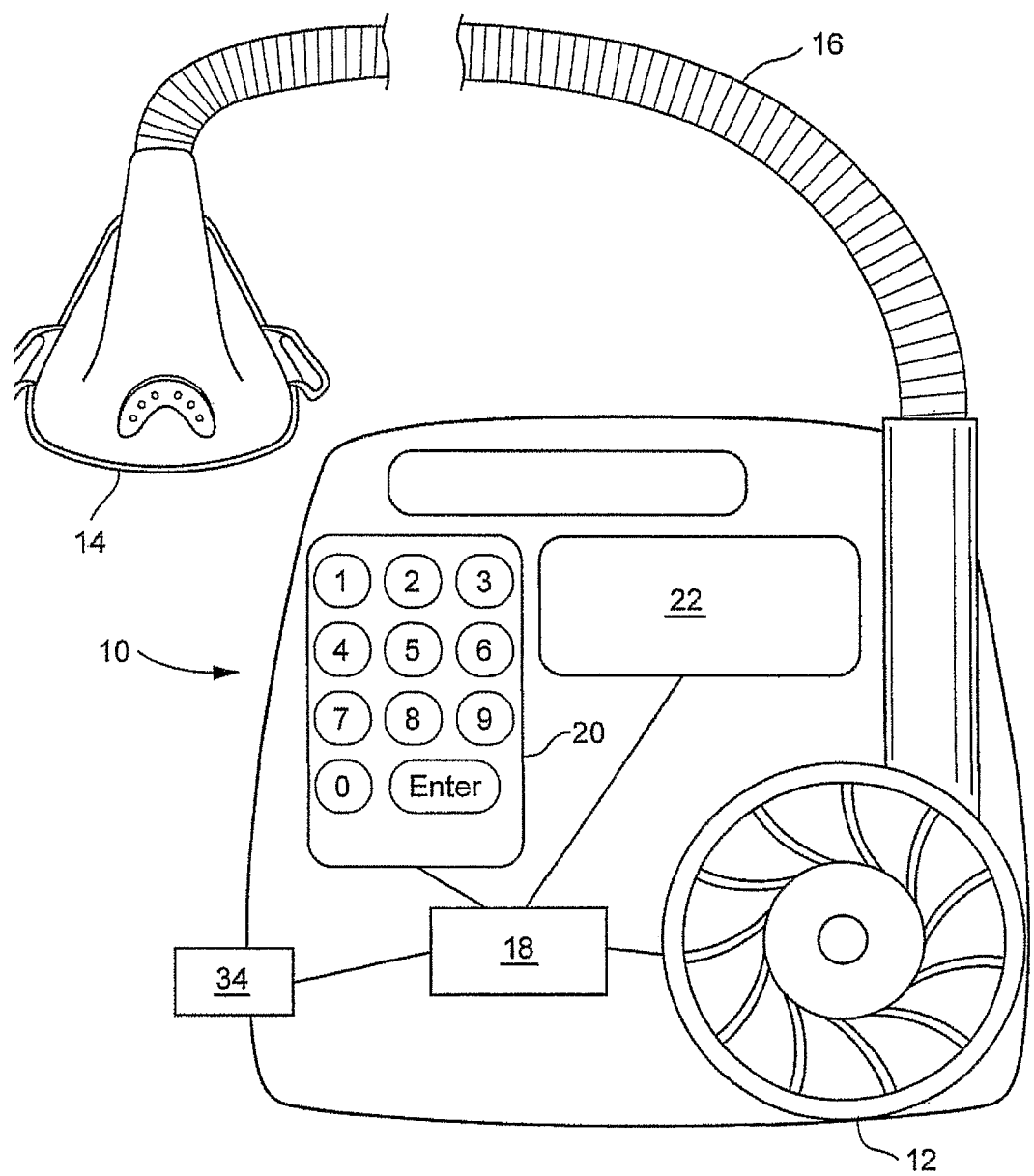
FIG. 1 is a perspective view of an exemplary flow generator.

The concepts of the present invention are suitable for any flow generator providing NIPPV and/or CPAP treatment, including but not limited to flow generators having motor controlled pressure regulation or valve pressure regulation. An exemplary flow generator structure will be described with reference to FIG. 1 for purposes of explanation.

A flow generator 10 includes a motor 12 that provides a supply of pressurized air for the administration of NIPPV and/or CPAP treatment. The pressurized air is delivered to a patient via a patient interface 14. An air delivery conduit 16 is coupled between the flow generator 10 and the patient interface 14. The patient interface 14 may have any suitable configuration as is known in the art, e.g., full-face mask, nasal mask, oro-nasal mask, mouth mask, nasal prongs, etc. Furthermore, the patient interface 14 also encompasses both vented and non-vented masks and dual limb mask systems. A processor 18 controls the operations of the flow generator. The flow generator is provided with a user interface unit or "communication system" 20 (which is generically intended to encompass both input and output systems of any suitable structure) to allow information input and a display unit 22 to display output information.

Communication System

Figure 2:
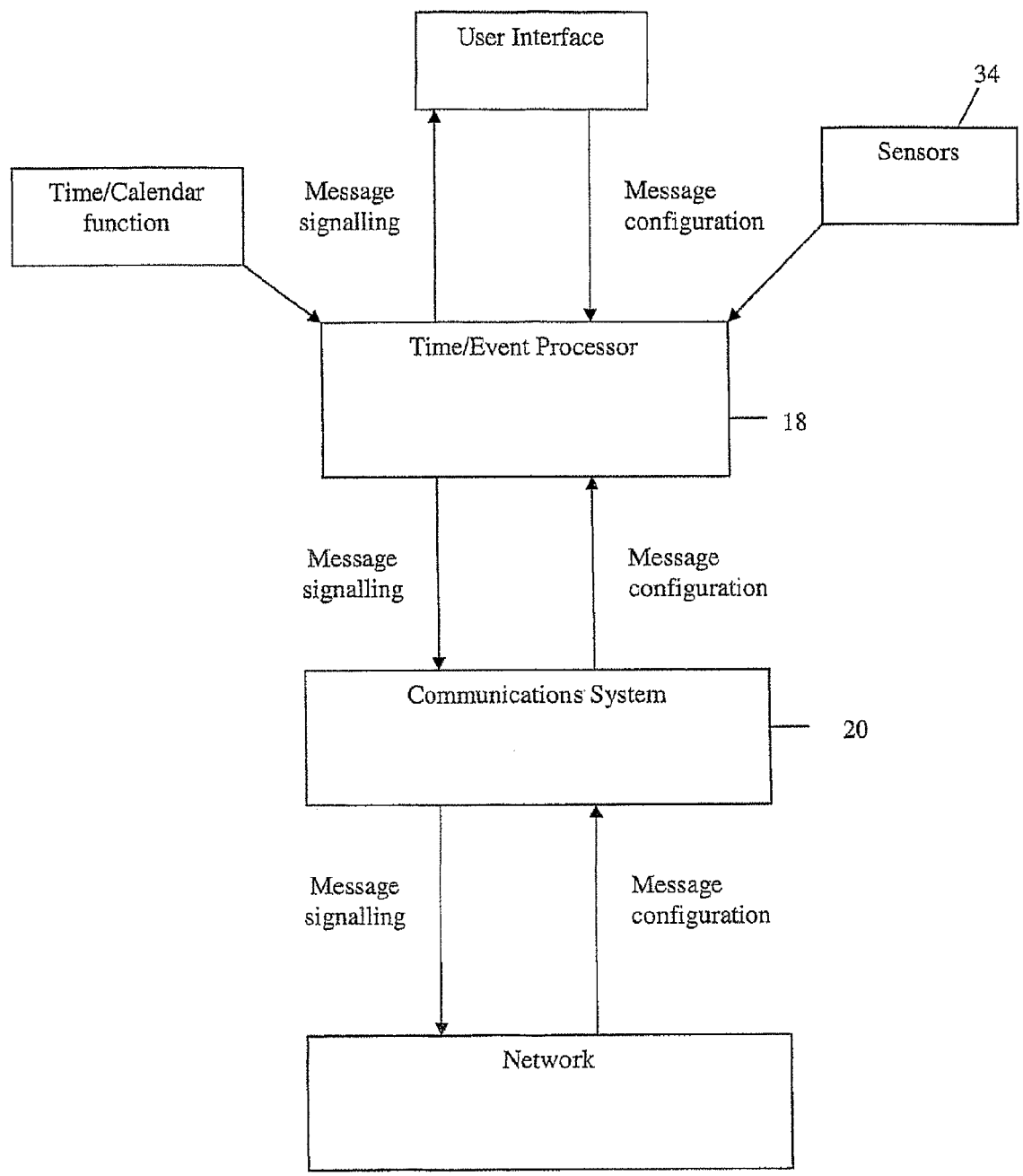
FIG. 2 is a schematic block diagram of the flow generator operating system and message/alarm functionality.

With reference to FIG. 2, the processor is coupled with the operation sensors (shown schematically at 34) and communication system 20. The processor is programmed to generate time-based or event-based messages relating to one or more of flow generator operation, flow generator service, flow generator use, patient health, peripheral devices and services, patient treatment, and general reminders or the like. The user interface or communications system 20 includes structure that effects delivery of the messages. Delivery of messages may be via the display unit 22 or via an external communication device such as a modem or wireless technology such as cellular telephony or via the internet through a network interface. With a remote communication system, the flow generator can also deliver messages to a physician, a flow generator service provider, the patient, or the like.

Time-Based Messages

The messages generated by the processor 18 may be time-based or event-based or both. Time-based messages are generated at predetermined time intervals based on either time of use or elapsed time. Examples of time-based messages include general reminders, where the processor is programmed to receive a reminder request input, and the messages comprise reminders generated at a time specified in the reminder request input. Examples of other time-based messages may include a notice that one or more parts should be replaced (after a certain period of use), a reminder concerning timing for a patient to schedule an appointment with their physician, a wake-up alarm, which may be an audible alarm or may be effected via the delivery of breathable gas to the patient such as via pulses of air or by pressure variations, and the like. The time-based messages may be customizable by the patient for use as a personal reminder. For example, the flow generator may be programmed to remind the patient to take their pills. Advertisements may also be generated at predetermined time intervals, possibly in relation to a time interval when a part such as the mask or filter should be replaced.

The time-based messages may also include helpful user tips to assist the user in maximizing flow generator functionality. A calendar and clock function enables use of the system to generate wake-up alarms as well as provide time-based messages based on either time of use or elapsed time. An example of a flow generator including a built in alarm clock is disclosed in U.S. patent application Ser. No. 60/703,432, filed Jul. 29, 2005, the contents of which are hereby incorporated by reference. Helpful tips and other use information can thus be provided to the patient based on the time of year. For example, the processor may be programmed such that it knows winter months are approaching (i.e., from the calendar) and can remind the patient to utilize their humidifier. In addition, the calendar and clock function can monitor user sleep cycle and awaken the user at non-REM sleep.

Event-Based Messages

Event-based messages are generated based on signals from the operation sensors 34 and are correlated to particular events or triggers detected by the processor 18 via the sensors 34. For example, the event-based messages may relate to flow generator parts requiring replacement or repair. The processor 18 can determine via the sensors 34 whether a particular part needs replacement or repair. For example, if a leak is detected in the mask, it may be that the mask needs to be replaced. The system may effect automatic ordering of one or more of the parts requiring replacement or generate a request for service or repair, which may be part of a user subscription. In concert with such a determination, the processor 18 may generate helpful tips to assist the user in properly positioning/wearing the mask. The processor 18 may generate advertisements as event-based messages, for example when parts need replacement or as new parts/products become available. In this context, the communication system 20 may be capable of receiving data as message content for example via the global network through the network interface. In this manner, the message content may include information relating to new products and peripherals cooperatively usable with the flow generator.

Peripheral Devices

The flow generator may additionally include peripheral devices providing enhanced functionality. In this context, the peripheral devices may be detected via an identifier including an identifying element providing an identifying feature unique to a specific peripheral component attachable to the flow generator. The processor 18 discerns the specific peripheral component via the identifying feature. This concept is described in detail in commonly-owned U.S. Patent Application Ser. No. 60/656,880, the contents of which are hereby incorporated by reference. In this manner, the messages generated by the processor 18 may relate to use and operation of the peripheral devices.

Notice Levels

In one embodiment, the event-based messages include notice levels relating to flow generator operation. The notice levels are changed based on a use condition duration detected by the sensors 34. For example, a use condition may be a leak at the mask. In this context, a first notice level may include an indication that the leak has been detected, a second notice level may include another indication that the leak has been detected along with user tips to correct the leak, and a third notice level may include a communication notifying a service provider or physician of the leak.

AHI Threshold

A patient's specific AHI (apnea-hypopnea index) threshold may be entered into the device and monitored as an indicator of the effectiveness of the therapy. AHI is a measure of the number of apnea or hypopnea events that occur per hour of sleep, which is used to assess the severity of sleep disordered breathing (SDB). Commonly, an AHI of 5 or greater is considered to indicate mild OSA. Thus the AHI will vary amongst different patients, and consequently an AHI threshold will also vary between patients. The AHI threshold may be determined and entered by a clinician for an individual patient. The AHI or AHI threshold is an example of an event that may be monitored and reported on using the messaging system of the present invention. A change in the AHI index may be considered an indicator of how effective the therapy has been. For example a decrease in the AHI would indicate that the therapy was having a positive effect.

Monitoring System

A remote monitoring system is described in the U.S. patent application Ser. No. 10/934,540, the contents of which are hereby incorporated by reference. This system is not present in the flow generator but is a patient server comprising a database of rules governing payment of home care devices and the details for patients and devices. The system monitors when a patient is eligible to receive payment for further home care devices and may generate a reminder letter to send to the patient; thus reminding and encouraging patients to update their devices. The system may also be used to monitor drug prescription requirements. This type of reminder may also be included in the present application such that the reimbursement or payment details for a patient are entered into the device or may be selected from a list, and then in a similar manner the device will remind the patient when they are eligible to purchase further equipment.

CONCLUSION

The flow generator of the invention includes a message generating capability and communication structure that facilitate and enhance its use. The ability to communicate information to the user will reduce users' needs to contact the physician or product supplier with questions. The system can record events thereby reducing the burden and therefore labor and costs for processing insurance coverage. A calendar and clock function enables use of the system to generate wake-up alarms as well as provide time-based messages based on either time of use or elapsed time. Sensors enable the system to generate event-based messages. Of course, the examples described herein are exemplary, and those of ordinary skill in the art will appreciate that many variations of messages may be generated by the flow generator of the invention, and the invention is not necessarily meant to be limited to the described examples.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention.

The invention claimed is:

1. A flow generator for delivering breathable gas to a patient, the flow generator comprising a processor coupled with operation sensors and a user interface, wherein the processor is programmed to generate at least one of time-based messages, event-based messages, or both time- and event-based messages relating to at least one of flow generator operation, flow generator service, flow generator use, patient health, peripheral devices and services, patient treatment, and reminders, wherein the time-based messages are generated at predetermined time intervals based on either time of use or elapsed time, and wherein the event-based messages are generated based on signals from the operation sensors, the user interface being configured to deliver the messages to at least one of a display, a flow generator service provider, the patient and a physician.

2. A flow generator according to claim 1, wherein the processor is programmed to receive a reminder request input, and wherein the time-based messages comprise reminders generated at a time specified in the reminder request input.

3. A flow generator according to claim 1, wherein the user interface comprises a wireless communication system, the wireless communication system communicating with at least one of a preset telephone number, a cellular phone, a pager, and a call center.

4. A flow generator according to claim 1, wherein the user interface comprises a network interface, the network interface delivering the messages via a global network.

5. A flow generator according to claim 4, wherein the event-based messages comprise messages relating to flow generator parts requiring replacement or repair.

6. A flow generator according to claim 5, wherein the event-based messages automatically order at least one of the parts requiring replacement and service for the repair.

7. A flow generator according to claim 4, wherein the network interface is configured to receive message content via the global network.

8. A flow generator according to claim 7, wherein the message content comprises information relating to new products and peripherals cooperatively usable with the flow generator.

9. A flow generator according to claim 1, further comprising a memory that stores software executed by the processor and data relating to flow generator use and operation, the processor executing the software to generate the messages.

10. A flow generator according to claim 9, wherein the memory comprises a data card.

11. A flow generator according to claim 1, further comprising peripheral devices providing enhanced functionality, the peripheral devices communicating with the processor, wherein the time-based and event-based messages relate to use and operation of the peripheral devices.

12. A flow generator according to claim 1, wherein the time-based messages are customizable.

13. A flow generator according to claim 12, wherein the time-based messages comprise a personal reminder for the patient.

14. A flow generator according to claim 12, wherein the time-based messages comprise a wake-up alarm.

15. A flow generator according to claim 14, wherein the wake-up alarm is an audio message.

16. A flow generator according to claim 14, wherein the wake-up alarm is effected via the delivery of breathable gas to the patient.

17. A flow generator according to claim 1, wherein the event-based messages comprise messages relating to a patient's AHI, wherein the messages are generated if the AHI exceeds a predetermined threshold or if the AHI deviates by a predetermined amount from an original setting or measurement.

18. A flow generator according to claim 1, wherein the time-based and event-based messages comprise advertisements.

19. A flow generator according to claim 18, wherein the advertisements are generated at predetermined time intervals.

20. A flow generator according to claim 18, wherein the advertisements are generated upon the occurrence of at least one event relating to flow generator use and operation.

21. A flow generator according to claim 1, wherein the time-based and event-based messages comprise messages relating to helpful user tips.

22. A flow generator according to claim 1, wherein the event-based messages comprise notice levels relating to flow generator operation, the notice levels being changed based on a use condition duration detected by the sensors.

23. A flow generator according to claim 22, wherein the use condition is a leak, and wherein a first notice level comprises an indication that the leak has been detected, a second notice level comprises another indication that the leak has been detected along with user tips to correct the leak, and a third notice level comprises a communication notifying a service provider or physician of the leak.

24. A CPAP apparatus comprising:
a flow generator that generates a supply of pressurized air to be provided at an outlet;
a patient interface engageable with a patient's face to provide a seal; and
an air delivery conduit coupled between the flow generator and the patient interface to deliver the supply of pressurized air from the flow generator to the patient interface,
wherein the flow generator comprises a processor coupled with operation sensors and a communication interface, wherein the processor is programmed to generate at least one of time-based or event-based messages relating to at least one of flow generator operation, flow generator service, flow generator use, patient health, peripheral devices and services, patient treatment, and reminders, wherein the time-based messages are generated at predetermined time intervals based on either time of use or elapsed time, and wherein the event-based messages are generated based on signals from the operation sensors, the communication interface being configured to deliver the messages to at least one of a display, a flow generator service provider, the patient and a physician.

25. An identifier for use with a flow generator that generates a supply of pressurized air to be provided at an outlet to a patient for treatment, the flow generator including a processor coupled with operation sensors and a user interface, wherein the processor is programmed to generate either time-based or event-based messages relating to at least one of flow generator operation, flow generator service, flow generator use, patient health, peripheral devices and services, and patient treatment, wherein the time-based messages are generated at predetermined time intervals based on either time of use or elapsed time, and wherein the event-based messages are generated based on signals from the operation sensors, the identifier comprising an identifying element providing an identifying feature unique to a specific peripheral component attachable to the flow generator, the processor discerning the specific peripheral component via the identifying feature, wherein the time-based and event-based messages are generated based on use and operation of the specific peripheral component.

26. A flow generator for delivering breathable gas to a patient, the flow generator comprising a processor coupled with operation sensors and a communication system, wherein the processor is programmed to generate at least one of time-based or event-based messages relating to at least one of flow generator operation, flow generator service, flow generator use, patient health, peripheral devices and services, patient treatment, and reminders, wherein the time-based messages are generated at predetermined time intervals based on either time of use or elapsed time, and wherein the event-based messages are generated based on signals from the operation sensors, the communication system being configured to deliver the messages internally and remotely.

27. The flow generator of claim 1, wherein the processor is further programmed to:
   monitor a sleep cycle of the patient; and
   based on monitoring the sleep cycle, cause the patient to be awakened during a non-REM sleep stage via the time based-message.

28. The flow generator of claim 1, wherein the processor is further programmed to:
   generate a first event-based message that is based on detection of a particular event or trigger; and
   generate a second event-based message that is increased in severity compared to the first-event-based message in accordance with a subsequent detection of the event or trigger.

29. The flow generator of claim 28, wherein the particular event or trigger is a use condition.

30. The flow generator of claim 28, further comprising a display unit that is configured to display an indicator of the first and/or second event-based message.

31. The flow generator of claim 28, wherein the generated first and/or second event-based message are delivered to the patient via variations in the generated supply of breathable gas.

32. A flow generator for use with a continuous positive airway pressure (CPAP) system or a non-invasive positive pressure ventilation (NIPPV) system, the flow generator comprising:
   a motor configured to generate a supply of breathable gas to a patient at a pressure elevated above atmospheric pressure, typically in the range 3-20 cm $H_2O$;
   at least one operation sensor to generate signals; and
   a processor to control flow generator operations, the processor configured to:
      correlate the signals of the at least one operation sensor to a particular event or trigger;
      initiate a first response when the particular event or trigger is first correlated with the signals; and
      initiate a second response that is changed from the first response based on the re-occurrence or the duration of the correlated particular event or trigger.

33. The flow generator of claim 32, wherein the particular event or trigger is a use condition.

34. The flow generator of claim 33, wherein the use condition is a leak.

35. The flow generator of claim 34, wherein the leak a mask leak.

36. The flow generator of claim 34, wherein the first response includes an indication that the leak has been detected.

37. The flow generator of claim 36, wherein the second response includes another indication regarding the leak.

38. The flow generator of claim 32, wherein the first response is associated with a first generated message and the second response is associated with a second generated message.

39. The flow generator of claim 38, wherein the first and second generated messages relate to CPAP/NIPPV flow generator operation, CPAP/NIPPV flow generator use, health of a patient receiving CPAP/NIPPV, and/or CPAP/NIPPV for a patient.

40. The flow generator of claim 32, further comprising a display unit that is configured to display information.

41. The flow generator of claim 40, wherein the output information includes a displayed indication of the first and/or second response.

42. The flow generator of claim 32, wherein a specific peripheral component is attachable to the flow generator, the specific peripheral component associated with an identifier including an identifying element that provides an identifying feature that is unique to the specific peripheral component,
   wherein the processor is further configured to discern the specific peripheral component via the identifying feature.

43. The flow generator of claim 42, wherein the initiated first and/or second responses relate to use and operation of the specific peripheral device.

44. The flow generator of claim 32, wherein the initiated first and/or second response is associated with variations in the generated supply of breathable gas.

45. The flow generator of claim 32, wherein the processing system is further configured to receive input of an apnea-hyopnea index (AHI) threshold.

46. The flow generator of claim 45, wherein the initiated first or second response is based on the AHI threshold.

47. The flow generator of claim 32, wherein the processor is further configured to:
   monitor a sleep cycle of the patient; and
   based on monitoring the sleep cycle, cause the patient to be awakened during a non-REM sleep stage.

48. The flow generator of claim 32, further comprising a data card that is configured to be removably attachable and provide data for operation of the flow generator.

49. The flow generator of claim 32, wherein the processor is further configured to:
   generate at least one time based message; and
   output the at least one time based message to a display, a service provider, the patient, and/or a physician.

50. The flow generator of claim 32, wherein the change from the first response is an escalation from the first response.

51. The flow generator of claim 32, further comprising a built-in clock that is configured to provide a time-based message to the patient.

52. A CPAP apparatus comprising:
   a flow generator according to claim 32; and
   an air delivery conduit adapted to be coupled to the flow generator.

53. The CPAP apparatus of claim 52, further comprising a patient interface that is configured to sealingly engage with the patient's face and adapted to be coupled to the air delivery conduit to thereby facilitate delivery of the breathable gas from the flow generator to the patient.

54. A flow generator of a continuous positive airway pressure (CPAP) system or a non-invasive positive pressure ventilation (NIPPV) system that is configured to deliver a supply of breathable gas to a patient at between 3 cm and 20 cm, the flow generator comprising:
   at least one operation sensor to generate signals; and
   at least one processor for controlling operations of the flow generator, the at least one processor configured to:
      receive signals that are generated by the at least one operation sensor;
      monitor the received signals to detect at least a first indication and a second, subsequent, indication that are related to a particular event or trigger;
      generate a first response in accordance with the detected first indication of the particular event or trigger; and
      generate a second response in accordance with the detected second indication of the particular event or trigger, the second response having an severity level that is greater than a severity level of the first response.

55. The flow generator of claim 54, wherein the particular event or trigger is a use condition.

56. The flow generator of claim 54, further comprising a display unit that is configured to display a visual indication of the first and/or second response.

57. The flow generator of claim 54, wherein the generated first and/or second response are delivered to the patient via variations in the supply of breathable gas.

58. The flow generator of claim 54, wherein the generated first and/or second response are event-based messages that are delivered to the patient.

* * * * *

UNITED STATES PATENT AND TRADEMARK OFFICE
CERTIFICATE OF CORRECTION

PATENT NO. : 8,424,514 B2  Page 1 of 1
APPLICATION NO. : 12/067234
DATED : April 23, 2013
INVENTOR(S) : Oates et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1368 days.

Signed and Sealed this
Eighth Day of September, 2015

Michelle K. Lee
*Director of the United States Patent and Trademark Office*